(12) United States Patent
Haucke et al.

(10) Patent No.: US 7,976,368 B2
(45) Date of Patent: Jul. 12, 2011

(54) METHOD AND DEVICE FOR PROCESSING FISH, POULTRY, OR OTHER MEAT PRODUCTS TRANSPORTED IN MULTITUDE ALONG A PROCESSING LINE

(75) Inventors: Hartmut Haucke, Meerbusch (DE); Ralph Anderson Miller, Lübeck (DE); Paul M. Hearn, St. John's (CA); Shawn Nicholas, Lee's Summit, MO (US)

(73) Assignee: Nordischer Maschinenbau Rud. Baader GmbH + Co. KG, Luebeck (DE)

( * ) Notice: Subject to any disclaimer, the term of this patent is extended or adjusted under 35 U.S.C. 154(b) by 93 days.

(21) Appl. No.: 12/444,369

(22) PCT Filed: Oct. 6, 2006

(86) PCT No.: PCT/EP2006/009682
§ 371 (c)(1),
(2), (4) Date: Apr. 3, 2009

(87) PCT Pub. No.: WO2008/043370
PCT Pub. Date: Apr. 17, 2008

(65) Prior Publication Data
US 2010/0029187 A1 Feb. 4, 2010

(51) Int. Cl.
*A22C 25/04* (2006.01)
(52) U.S. Cl. .................................................. 452/184
(58) Field of Classification Search .............. 452/177, 452/182–184
See application file for complete search history.

(56) References Cited

U.S. PATENT DOCUMENTS

| | | | | |
|---|---|---|---|---|
| 4,209,878 A | * | 7/1980 | Albert | 452/134 |
| 4,217,679 A | * | 8/1980 | Gordon | 452/140 |
| 5,205,777 A | * | 4/1993 | Hohenester | 452/142 |
| 5,215,772 A | * | 6/1993 | Roth | 426/231 |
| 5,352,153 A | * | 10/1994 | Burch et al. | 452/157 |

(Continued)

FOREIGN PATENT DOCUMENTS

DE 35 24 906 2/1986

(Continued)

OTHER PUBLICATIONS

Form PCT/ISA/220 International Search Report issued in corresponding application PCT/EP2006/009682, dated Jan. 27, 2007.

(Continued)

*Primary Examiner* — Thomas Price
(74) *Attorney, Agent, or Firm* — Venable LLP; Robert Kinberg; Steven J. Schwarz

(57) ABSTRACT

In a method for the processing of fish, poultry or other meat products being conveyed in a plurality along a processing line, components which are to be excluded from consumption are separated and edible products obtained as a result for consumption are checked with an automatic inspection device for residues left behind. Separation takes place in such a way that, in the case of a number of edible products, minimized residues of at least one kind are deliberately permitted and induced for further processing of the edible products, in particular to optimize the edible product recovery. The automatic inspection device is adjusted to detect the minimized tolerance residues, and inspected edible products with and without the tolerance residues are separated from each other. In an apparatus for carrying out the method, a separating device with at least one separating tool is designed in such a way that, in the case of a number of edible products, minimized tolerance residues of at least one kind are left behind for further processing of the edible products, and the inspection device is connected to a separator device which distinguishes edible products with and without residues according to the inspection results and discharges them separately from each other.

35 Claims, 4 Drawing Sheets

U.S. PATENT DOCUMENTS

| | | | |
|---|---|---|---|
| 5,428,657 | A | 6/1995 | Papanicolopoulos et al. |
| 5,847,382 | A | 12/1998 | Koch et al. |
| 5,937,080 | A | 8/1999 | Vogeley, Jr. et al. |
| 6,532,064 | B1 | 3/2003 | Hearn et al. |
| 6,546,304 | B2 | 4/2003 | Thorvaldsson et al. |
| 6,558,242 | B2 * | 5/2003 | Veldkamp et al. ............ 452/134 |
| 6,563,904 | B2 * | 5/2003 | Wijts et al. ...................... 378/58 |
| 6,970,757 | B1 | 11/2005 | Hewett et al. |
| 6,983,678 | B2 | 1/2006 | Wattles et al. |
| 7,251,537 | B1 * | 7/2007 | Blaine et al. .................... 700/29 |
| 7,452,266 | B2 * | 11/2008 | Bottemiller .................. 452/150 |
| 7,476,150 | B2 * | 1/2009 | Ilch et al. ...................... 452/198 |
| 7,621,806 | B2 * | 11/2009 | Bottemiller et al. .......... 452/150 |
| 7,654,890 | B2 * | 2/2010 | Ilch et al. ...................... 452/150 |
| 2003/0098409 | A1 | 5/2003 | Bond et al. |
| 2004/0267396 | A1 | 12/2004 | Coppola et al. |

FOREIGN PATENT DOCUMENTS

| | | | |
|---|---|---|---|
| EP | 0 128 889 | | 12/1984 |
| EP | 0 819 381 | A1 | 1/1998 |
| EP | 1 004 242 | A1 | 5/2000 |
| EP | 1 087 280 | A2 | 3/2001 |

OTHER PUBLICATIONS

Form PCT/ISA/237 Written Opinion for corresponding application PCT/EP2006/009682, dated Jan. 27, 2007.

European Patent Office Opposition issued in related European Application No. 06806087.0 on Feb. 24, 2011.

"High-Tech Processing at SPE Seafood Processor," Tom Wray, Seafood International, Jan. 1, 2004.

"Up and Running—The New Pinbone Removal and Detection Line at Samherji," Marel case study 104.10, May 2003.

"Pinbone Picking With SensorX," Seafood International, May 1, 2005, (http://www.intrafish.no/fni/news/article191632.ece).

\* cited by examiner

METHOD AND DEVICE FOR PROCESSING FISH, POULTRY, OR OTHER MEAT PRODUCTS TRANSPORTED IN MULTITUDE ALONG A PROCESSING LINE

BACKGROUND OF THE INVENTION

The invention concerns a method and an apparatus for the processing of fish, poultry or other meat products being conveyed in a plurality along a processing line. This involves meat products which have inedible components or components which are to be excluded from consumption and separated (components to be separated). It is known that meat products obtained by separation, namely fillets, can be checked. with an automatic inspection device for defects left behind, namely bone residues in fish fillets or poultry fillet pieces.

For example, it is known that fish fillets from which pin-bones have been separated can be inspected with a sensor device for detecting pin-bone residues left behind. Fish fillets which have pin-bone residues are delivered to an inspection station in which the bone residue is indicated on a display, in order to be removed manually by processing personnel. The inspection results are also used to obtain information on the product quality.

When filleting fish and meat products, a higher yield of flesh is obtained by making cuts closer to the bone. However, this is associated with the uncertain risk that dangerous hidden bone residues, for example of the wishbone in poultry or the collar bone in fish, or areas contaminated with them will be left behind unchecked in the fillet (edible product). This situation is aggravated for example if bone splinters and/or haematomas arise during slaughter. To reduce the risk of bones, processing staff therefore endeavour to adjust their manual or automated filleting machines in such a way that if possible the whole of the bone/contaminated area is separated. As a result, the yield for obtaining fillets is impaired because defect-free flesh is also cut away to an unwanted extent.

For deboning or filleting front halves of poultry, machines which separate the poultry breast using computer-controlled cutting knives and scraper blades are known. The separated poultry breast pieces (edible products) are taken by a conveyor belt to a station at which workers check the fillets manually for bone residues and also remove them manually. It is usual then to subject the fillets which have been found to be defect-free and separated to a final inspection which is carried out manually or by means of an X-ray device.

In order to debone fillets practically without residues and remove bone components from them, it is precisely in conjunction with an automatic inspection with respect to maximum reliability for the removal of defective residues that it will be appropriate to carry out manual trimming following automatic inspection by personnel. Naturally it is important that the activity of trimming can be made as simple and reliable as possible in order to make it easier and safer and if necessary also reduce requirements of personnel qualifications. For this purpose auxiliary devices which show fillets that have bone residues on a monitor to facilitate trimming are known. Even such auxiliary systems with monitors can lead to personnel fatigue or inattentiveness if defect residues occur at relatively long intervals, particularly irregularly and/or with considerable variation in appearance.

SUMMARY OF THE INVENTION

Hence aims of the invention consist of providing a method and an apparatus designed therefor, for detecting and removing residues that occur during separation, in particular during filleting, with high efficiency and maximum reliability in the case of edible products. If manual processing and/or checks are carried out in the overall process, these activities are to be simplified with respect to the choice or hire of personnel as well, and automatic and controlled processing are to be capable of being carried out and improved. The method with suitable apparatus is also intended to open up a broad spectrum of applications, namely to be usable for any kind and form of fish, poultry or other meat products. That is to say, in particular a method is to be obtained which can be carried out on the one hand for components with very different properties, structure and composition (texture) to be separated and on the other hand for meat products in raw, half-finished or finished form, i.e. for example also for meat that has been roasted or otherwise prepared for consumption or shaped meat mass.

The aims of the invention are achieved by a special method and an apparatus designed therefor. Thus the invention is defined by a method for the processing of fish, poultry or other meat products of any kind and form being conveyed in a plurality along a processing line, which contain inedible components or components which are to be excluded from consumption and separated (components to be separated) of at least one kind, in which the components to be separated are separated from the meat products, and edible products obtained as a result for consumption are checked with an automatic inspection device for residues left behind during separation, comprising the following steps: i) the components to be separated are separated from the meat products in such a way that, in the case of a number of edible products, minimised residues of at least one kind are permitted and induced for further processing of the edible products, in particular to optimise the edible product recovery; ii) the automatic inspection device is adjusted to detect the minimised tolerance residues and iii) edible products discharged by the inspection device and with and without the tolerance residues are separated.

An apparatus according to the invention provided for the method according to the invention comprises a separating device for separating inedible components or components which are to be excluded from consumption (components to be separated), an automatic inspection device mounted behind the separating device for checking the edible products obtained by separation for residues left behind, and a means mounted behind the inspection device for separating edible products with and without residues, the separating device with at least one separating tool being designed in such a way that, in the case of a number of edible products, minimised tolerance residues of at least one kind are left behind for further processing of the edible products, in particular to optimise the edible product recovery, that the automatic inspection device is adjusted to detect the minimised tolerance residues and connected to a separator device which distinguishes edible products with and without residues according to the inspection results of the inspection device and discharges them separately from each other.

It is peculiar to the invention, for separating the components to be separated in the case of a number of edible products, to bring about very deliberately a minimum of reduced residues. That is to say, residues are deliberately tolerated to a certain extent and for a number of identical edible products being conveyed in a plurality. This is how the term "tolerance residues" is to be understood. In essential contrast to ordinary adjustments for the separation of wishbones, collar bones, pin-bones, and so defective components which must not be contained in fillet pieces, the known adjustments consisting in that residual components are avoided as extensively as possible from the outset, according to the invention it was found that the defined tolerating of residual components delivers a number of particular advantages for processing particularly with respect to efficiency, safe removal of residues left behind (product safety) as well as product recovery and quality. Thus, with the admission of tolerance residues it is possible to preset and establish a controlled risk of residues or bones. As a result, the residual or defective location to be measured and determined is particularly qualified and quantified with respect to measurement and determination for inspection. It was found that the automatic inspection device can be particularly reliably and safely adjusted for the detection and determination of the permitted residues (tolerance residues). Hence separation of the edible products which are discharged by the inspection device and have the tolerance residues, from the residue-free edible products, is also particularly safe.

The high reliability of detection achieved is crucial and essential for subsequent separation. In particular there are advantages for separating the tolerance residues from the detected and separated edible products. Due to the tolerated residues, with the plurality of pieces of the same kind and corresponding shape to be processed along the processing line, these residues occur with a frequency which has a favourable effect on the activity of trimming by personnel. Also the pattern, namely the optical appearance of the tolerance residues (which are to be removed) is standardised or stabilised to a certain extent, also promoting manual processing. This also leads to the fact that the product line can be operated at a higher speed. With the measures according to the invention, in particular fish and poultry products in the natural state can be processed particularly effectively with respect to product recovery and quality as well as with respect to an optimum work cycle. Yet due to the measure according to the invention, whereby minimised product residues are deliberately left behind after separation, applications in which the minimised residues have quite different textures to bone residues can also be carried out. It is always important that a definite and hence qualified and quantified texture is deliberately tolerated for measurement and determination with the inspection device. Due to the range of variation in local appearance in the sequence of the plurality of identical products conveyed, with minimisation advantage is taken of the fact that some of the products are residue-free, while others of the products have the residues to be separated, distributed over the work cycle. Adjustment of the extent of minimised residues can appropriately be used to adjust the frequency of appearance of products with tolerated residues with regard to required processing. In any case a high product yield is obtained.

An advantageous embodiment of the invention lies in that, by means of the inspection device, at least one texture representing tolerance residues and if necessary at least one further substance texture of the edible products are measured, and at least one variable which represents qualitative, quantitative and/or local texture substance information of the edible products and is used to influence at least one separating process in front and if necessary at least one further processing step in front of and/or behind the inspection device, is determined. The minimisation of residues according to the invention acquires particular importance because by this means—with optimum recovery of residue-free meat or fish—on the one hand edible products which to a large extent have residues defined as minimal, and on the other hand those which are free from tolerated residues, are permitted deliberately.

For a given product, for example for front halves of poultry or breast caps of poultry which are conveyed in a plurality and are to be processed, it is appropriate and desirable to adjust the minimised residue dependent on the ratios actually occurring. This is achieved according to an embodiment of the invention by the fact that, by means of the inspection device, at least one texture representing tolerance residues is measured, and at least one associated variable which represents qualitative, quantitative and/or local texture substance information of the edible products and is used to influence at least one separating process in front of the inspection device, is determined. In order to optimise the whole of the processing, within the scope of the method according to the invention the inspection device can also be used to measure at least one further substance texture of the edible products and determine at least one associated variable in order to influence at least one further processing step in front of and/or behind the inspection device. As tolerated residues are left behind according to the invention, they can be provided deliberately for detection or measurement, and the inspection device which as such is a measuring and detecting device is adjusted to the texture of the tolerance residue to be detected. Consequently, tolerance residues of a very different nature and appearance can be detected, namely in particular those which have bones, gristle, blood vessels, fat, skin, membranes, bubbles, sinews, tissue, parasites, inclusions, structural/substance abnormalities and/or foreign bodies or the like. In addition to the adjustment and use of permitted tolerance residues according to the invention, one particular embodiment can also consist in that one or more textures to be inspected are determined by at least one meat area, at least one layer area, at least one bone area and/or a structure combining such areas.

In particular in order to adapt the separation of tolerated residues to the circumstances due to real-time measurement of the inspection device, but also in order if necessary to influence other processing steps, it proved particularly advantageous to make comparisons of nominal and actual values by predetermining at least one reference variable and/or ratio of reference variables in order to influence the respective measured processing step according to the standard(s). Appropriately, the preset variables are determined according to the characteristics of the meat product or edible product to be processed, processing parameters and/or personnel handling parameters.

Actual variables can be those which are calculated with a computer of the inspection device according to a program and/or algorithm, where appropriately average accumulations of measured values can be included. Averaging presupposes the tolerance residues that are permitted according to the invention.

Particularly advantageously, with the inspection device at least one variable representing the degree of edible product recovery (yield) can be determined and used to optimise recovery, by using the variable which represents the degree of recovery to control processing in front of the inspection device for optimally varying the aforementioned variable. In the example of one embodiment, fish products are skinned, the silver or fat layer representing the degree of recovery after skinning being measured with the automatic inspection device, and at least one corresponding variable being determined, which is used particularly according to a preset variable for adjustment of skinning to optimise edible product recovery.

Appropriately, to minimise the tolerance residues of edible products, at least one texture information variable is determined by means of a computer of the inspection device, which calculates the information variable(s) on the basis of measurements. It proved to be particularly advantageous that by means of the inspection device at least two texture information variables are determined, which are put in relation to each other to minimise the tolerance residues, at least one given ratio being preset so as to induce minimised tolerance residues. This method is carried out particularly advantageously and preferably by the fact that a texture information variable representing the tolerance residue and a texture information variable defined by an area which is at least partially free from tolerance residues, are determined on edible product with minimised tolerance residue. In this case it is appropriate that, with respect to one kind of product, a characteristic average product fraction of tolerance residues and an average residue-free fraction are defined in a preset distribution for a separating process which minimises the tolerance residues optimally, in the processing line in front of the inspection device. For such an embodiment, the inspection device is designed with a computer which calculates data on the distribution of tolerance residues in accordance with the current measurements on the edible products. For example, it is calculated in the inspection device at what average level in an edible poultry product wishbone residues occur, and at what average level meat occurs between ribs (rib meat). It was found that certain levels in each case represent an optimum separation of components to be separated, leaving the tolerance residues. If for example the inspection device determined on average a level of 20% of wishbone residues and a level of 75% of rib meat for a plurality of processed chicken breast fillets, it turned out that the separation process was set optimally with respect to the maximum yield (meat recovery). Within the scope of the invention, such an optimum setting is referred to as the sweet spot. A finding on which the invention is based therefore consists in that an optimum yield (meat recovery) is achieved during separation in front of the inspection device if bone residues are deliberately left or tolerated in relation to the meat recovered. As the inspection device with measuring/computer means is able to determine the tolerated residue as well as the proportion of meat or fish with maximum reliability, no drawbacks arise because the edible products with minimal residues are detected correspondingly safely and reliably and separated from the residue-free edible fillet products.

The optimum separating process according to the invention referred to as the "sweet spot" is predetermined in particular dependent on the product size, processing parameters, handling practices during loading and/or the product species (flock/shoal species) or the like. Accordingly, the "sweet spot" is different from one case to the next, and can be determined empirically to obtain the target variable. For instance, the above-mentioned 20% to 75% ratio is used as the nominal value with which the average actual value, measured and calculated with the inspection device, is compared in order thus to influence and adjust the separating process in such a way that the maximum efficiency ("sweet spot") is achieved.

In order to induce the "sweet spot" automatically according to a particularly preferred and appropriate embodiment of the invention, the method according to the invention is carried out in such a way that the components of the meat products to be separated are separated from the latter with an automatic separating device, and that the variables measured and determined by the inspection device are used in a feedback circuit to control the separating process to minimise the tolerance residues.

But the "sweet spot" can also be influenced dependent on the personnel or a worker who is employed to load the filleting/separating device in front of the inspection device and/or for trimming in the product line behind the inspection device, on the basis of different handling or manual skill. The "sweet spot" or the associated optimum ratio obtainable between tolerable residue (for example, wishbone residues) and meat recovered (for example, rib meat) is therefore determined from one case to the next. The inspection device is then adjusted in order to adjust and retain the individual "sweet spot"—in allocation to personnel. For example, in one case the tolerable residue is set higher than in another case because, during final manual trimming, the personnel work more carefully in the former case than in the latter case. Referred to the product yield over all processing operations, the yield with the individual "sweet spot" is then better for personnel in the latter case than in case of operation in which the "sweet spot" adjustment is made as in the former case.

The method according to the invention can be designed and carried out particularly advantageously if edible products with and without residues discharged by the inspection device are separated from each other automatically by the fact that the inspection device controls a separator device which extracts edible products with tolerance residues from a stream of inspected edible products. Extracted edible products with tolerance residues can be trimmed manually or automatically to separate the tolerance residues and returned to the product line from which they were extracted. In the case of automatic trimming, the measurements of the inspection device can be used in conjunction with computer control of the inspection device as control variables for trimming.

One particular embodiment of the method according to the invention also consists in that in the anatomical region of an edible product, e.g. a poultry fillet, the presence of tolerated residues—e.g. wishbone residues—and blood is measured with the inspection device in order to detect properties of the product which are influenced in this region by slaughter and optimise slaughter processing. Slaughter processing is then altered or improved to the effect that the appearance of haematomas is eliminated and any bone splintering is avoided.

An apparatus according to the invention is appropriately equipped with an inspection device which has at least one measuring/control means which measures tolerance residues or other substance texture areas and determines corresponding display and/or control variables. The above-mentioned means is appropriately equipped with an electronic computer or processor unit which calculates control variables according to a program or algorithm. Parameters for such calculations or settings can be determined in particular by the type and/or properties of the residues, by ratios of fractions with and without residues, and processing parameters and data which also include handling patterns or capabilities of operating personnel.

A control means or computer of this control means is appropriately also provided and connected in such a way that at least one processing step is controlled by a comparison of nominal and actual values, the nominal standard being determined in particular by characteristics of the meat product or edible product to be processed and/or processing parameters including handling peculiarities.

The inspection device in a preferred embodiment is designed with a measuring/control means with, if necessary, a computer-controlled means so as to detect tolerance residues and hence in combination an area of the edible products which is at least partially free from tolerance residues for control of the separating device in front of the inspection device with a view to optional minimisation of tolerance residues left behind. Preferably and appropriately, the inspection device is equipped with a measuring/control means which detects texture areas in a combined X-ray/optical measurement. For example, parts that do not show through such as in particular non-visible hidden bones and gristle are detected by means of the X-rays, while an optical measuring means detects textures that show through such as flesh, blood inclusions, parasites and the like and, if applicable, visible bones. It was found that, in particular with a combined measurement which has measurement sensors designed for different texture areas, essentially 100% detection can be achieved. This is of particular importance for the method according to the invention, which permits edible products/pieces with tolerated residues, for the detection of these residues.

In a particularly advantageous embodiment, the separating device in front of the inspection device is equipped with at least one separating tool that can be controlled by the inspection device, the inspection device being connected in a feedback circuit to the separating device to minimise the tolerance residues in accordance with a comparison of nominal and actual values. Appropriately, the inspection device is designed for the comparison of nominal and actual values in such a way that control takes place in accordance with a preset ratio between parts of the edible product with and without residues.

The inspection device is particularly advantageously and appropriately connected to a separator device in a control circuit, the separator device being arranged and designed to extract edible products with residues from the inspected stream of edible products. The separator device is appropriately equipped so as to be arranged and designed for the separation of tolerance residues in conjunction with at least one trimming device, the trimming device receiving edible products with residues which are separated by the separator device, and making them available after trimming for return to the product stream of the apparatus. According to an embodiment the trimming device can be equipped with a means for automatically separating the tolerance residues. Particularly advantageously, the automatic trimming device can be connected by a coupling circuit to the inspection device in such a way that trimming takes place in accordance with at least one property of the tolerance residue, meat product and/or edible product which is detected by the inspection device.

Subsidiary claims are aimed at the above and other appropriate and advantageous embodiments of the invention. Particularly appropriate and advantageous embodiments or possible forms of the invention are described in more detail with the aid of the following description of the practical examples shown in the schematic drawings:

DETAILED DESCRIPTION

Figure 1:
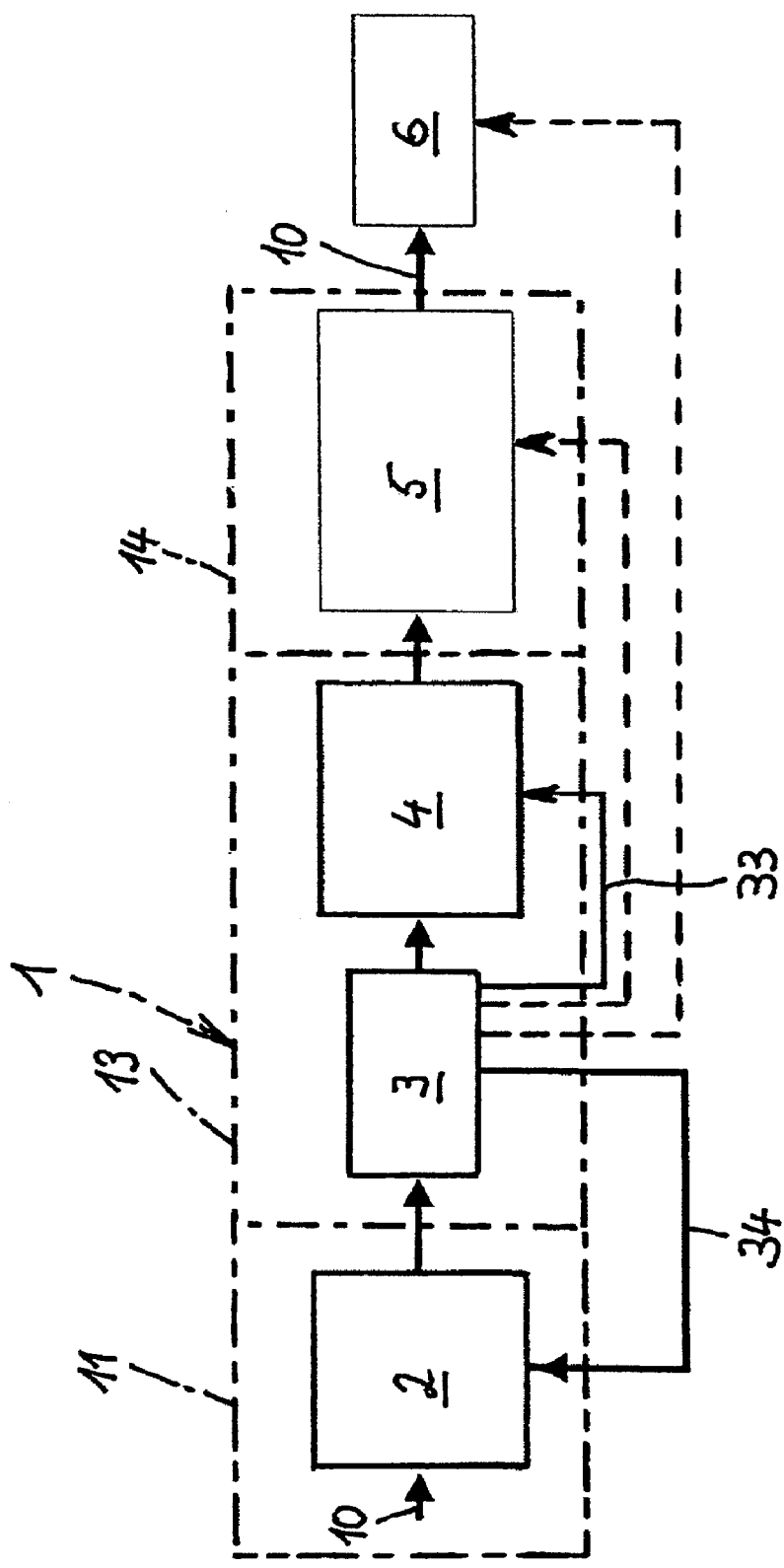
FIGS. 1 and 2 diagrams to show an apparatus according to the invention and a method according to the invention carried out with it, FIG. 3 in an axonometric view, a processing line according to the diagrammatic view in FIGS. 1 and 2, and FIG. 4 a diagram to show processing stations in conjunction with an automatic inspection device which is operated by the method according to the invention and is provided for the control of additional method cycles in connection with "sweet spot" control according to the invention.
Figure 2:
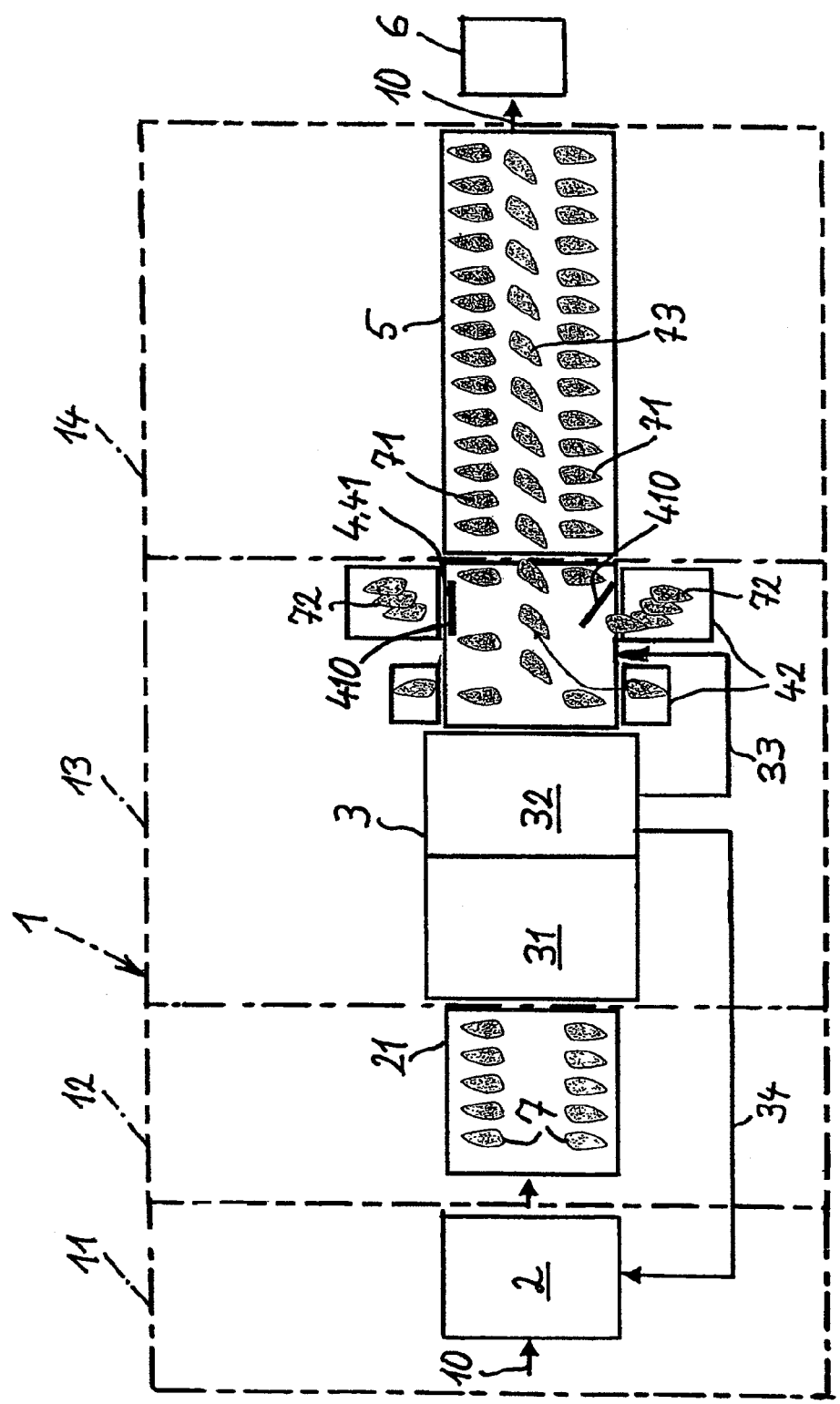
Figure 3:
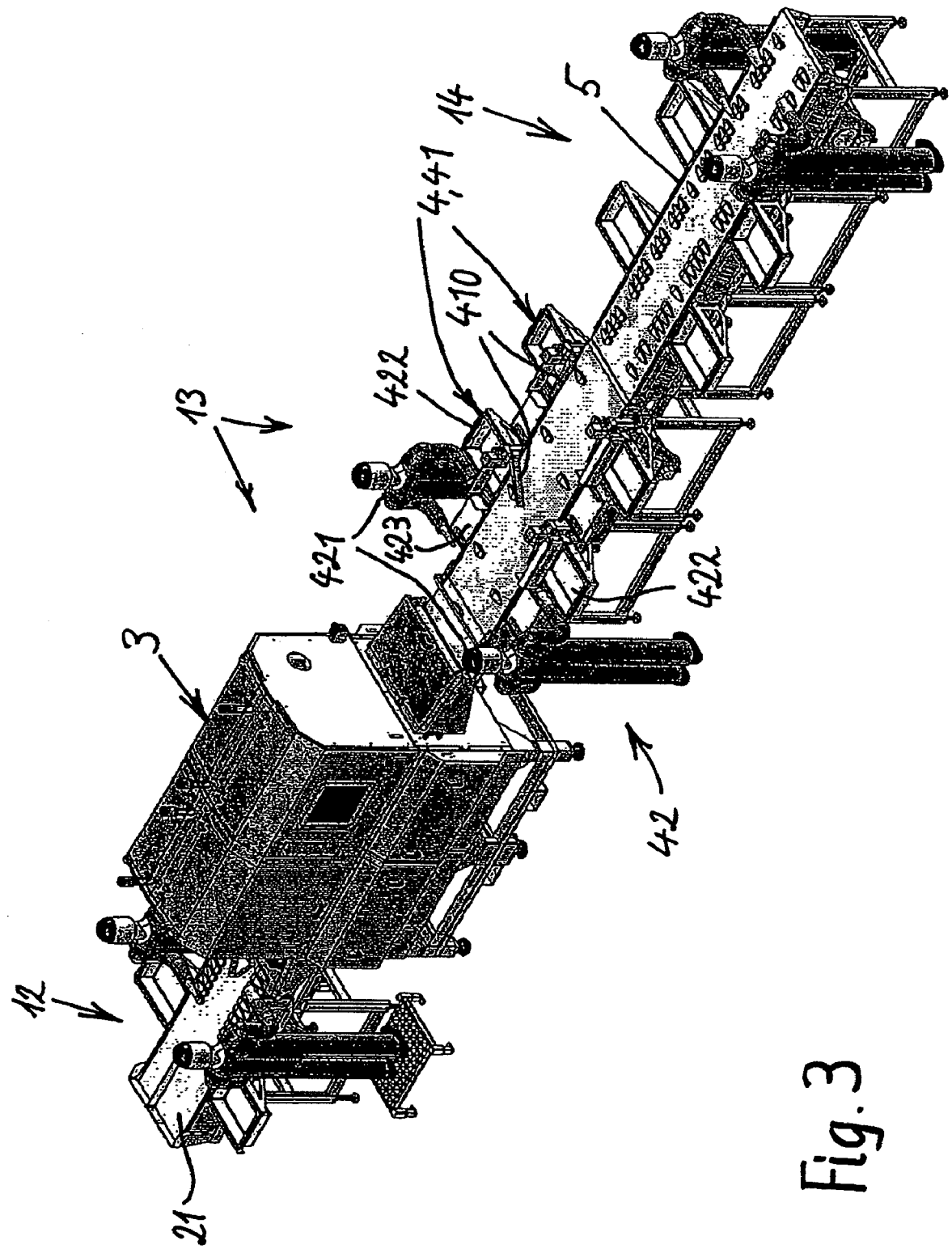

As can be seen from FIGS. 1, 2 and 3, an apparatus 1 according to the invention has sections 11, 12, 13 and 14 along a processing line 10. In the embodiment, front halves of poultry are filleted. In an automatic separating device 2 known per se, the front halves of poultry are held with holding devices, not shown, and transported. Components of the front half of poultry to be excluded from consumption are separated by the fact that the poultry breast to be recovered for consumption is removed using computer-controlled cutting knives and/or scraper blades, not shown. The edible poultry breast products 7 recovered are relinquished onto a conveyor 21 in the delivery section 12. There the edible products 7 (poultry breast fillet pieces) are placed on a horizontal processing surface and oriented in such a way that they do not overlap and the cut sides are directed upwards. The edible products 7 are then first conveyed in section 13 into an inspection device 3 along the line 10. There the edible products 7 lie cut side up, so that they can be checked from above for residues left behind in the separating device 2 during separation.

The inspected edible products 7 are discharged into section 13 in two rows parallel to the processing/transport line 10 and located on the outside on a conveyor. The two transport rows in section 13 are assigned a separating means 4 which is formed by a separator device 41 with ejector arms 410. The separating means 4 is wired and connected by an electric coupling circuit 33 to the inspection device 3 in such a way that edible products 72 which have defective residues are extracted from the stream of edible products 71 which the inspection device 3 has detected as free from residues, for additional trimming, namely, to separate the defective residues by means of a trimming device 42. The edible products 73 trimmed in this way are in the practical example introduced back into the processing line 10 in a conveying row between the rows of edible products 71. The edible products 71 or 73 which are then conveyed in three rows in section 14 with a conveyor are delivered to a size-sorting device 6 which automatically classifies the edible products 71, 73 according to size.

According to the invention, the separating device 2 and the inspection device 3 directly behind it are operated in such a way that, in the case of a number of edible products 7, minimised residues are permitted and induced for further processing of the edible products 7. In the practical example it is a question of designing the separating process in the separating device 2 with such precision in accordance with the inspection results of the separating device 2 that wishbone residues are permitted in the edible products (poultry breast pieces) 7 in section 12 to a given extent, the inspection device being designed and set for measuring and evaluation for these residues.

In section 14 a further check may be provided, by carrying out manual inspection there for detecting edible products with residues and manual trimming to separate the residues. As can be seen from FIG. 3, at the end of the conveying zone in section 14 a final manual inspection has also been provided for detecting edible products with residues. The end product is then conveyed to the automatic size-sorting device 6 for subsequent packing.

In the embodiment, according to the invention special adjustment and execution of the separating process in the separating device 2 are carried out by the fact that the inspection device 3 calculates defect distribution data on the basis of a combined measurement, and these results are used to adjust the separating process according to a preset distribution, that is, to perform control or regulation of nominal and actual values.

The inspection device 3 is equipped with a measuring means 31 which has on the one hand a sensor device for hidden or non-visible residues or residues that do not show through and on the other hand a sensor device for optically detectable residues. In the embodiment the measuring means 31 is equipped with an X-ray device which in any case almost 100% detects non-visible wishbone residues that are completely hidden. The optical sensor device detects brightness and/or colour differences. It is oriented and set so that it also at least almost completely detects the proportion of bone-free meat or fish, that is, the rib meat in the poultry breast piece. Appropriately, the optical measurement is in addition adjusted to measure visible bone residues or those that show through. According to the invention the measurements are performed on edible products 7 transported in a plurality along the processing line 10 through the inspection device 3 in such a way that, by evaluation and processing of the measurement results, average values or an average ratio for the proportions of wishbone residue and rib meat is obtained in a program-controlled process computer 32 known in the art.

For instance, it was found that a chicken breast which is separated from the front half of the poultry for filleting can be filleted with optimum quality and yield if on average a level of 20% of wishbone residues and a level of 75% of rib meat is measured. The separating process is then adjusted according to the invention in such a way that these average level ratios appear or are retained. Within the scope of the invention this optimum setting is referred to as the "sweet spot". The "sweet spot" setting can be determined empirically, and it depends on a number of factors which are determined by the meat product and processing and/or handling parameters or characteristics. In particular the "sweet spot" setting can be different from one processing system to the next, and so from one user to the next, or be adapted and adjusted precisely for the user and the system. The settings of the process computer 32 of the separating device 2 must be adjusted for example dependent on poultry size, flock/shoal species and handling practices. For example, allowance is also made for individual manual processing or handling. In particular utilisation of work capacity which is determined dependent on number and/or qualifications of the processing personnel along the processing line is included.

In particular it was found that, using a certain ratio of defective residue and defect-free fraction, there can also be optimisation with respect to residues which are not used to determine the residual ratio for the "sweet spot". The inspection device 3 used according to the invention measures and determines any kind of residues which are to be excluded from the edible product, and so in the embodiment from the poultry product fillet, that is, in particular residues which are not used for minimal tolerable residue adjustment. Here the suitability of the inspection device 3 for detecting residues or texture areas defining them completely and in any case with almost 100% reliability is in any case important. For this purpose the above-mentioned measuring system 3 which performs hybrid measurements is used, to detect very different textures equally reliably within a desired time window.

The method according to the invention is not confined to the use of an inspection measuring device with hybrid measurement. For example, it may be sufficient to detect the degree or level of a tolerated residue with one kind of measurement, e.g. with X-ray measurement. As far as the measuring system is able to determine a residue sufficiently on the basis of mere appearance without visual detection, the edible products to be checked do not have to be specially aligned for loading of the inspection device 3.

With determination of the solids (bone) or other residue fractions or residue-free fractions, a standard is obtained for a risk of bone which is determined by the process computer 32 of the inspection device 3. Naturally the aim is to minimise the risk of bone. But according to the invention a risk of bone is deliberately permitted in order thus to obtain the basis and standard for "sweet spot" optimisation.

The process computer 32 of the inspection device 3 is supplied with the desired characteristic or application-related nominal data for the comparison of nominal and actual values described above. These data are entered in the computer. In the embodiment of FIGS. 1 and 2, the separating device 2 is automated and can be controlled by means of the inspection device 3. For this purpose the computer 32 of the inspection device 3 is connected in a feedback circuit 34 to the separating device 2. In this way the cutting operation or any other division suitable for separation, even without cutting, in the separating device 2 can be optimally adapted to the actual circumstances in order to retain the "sweet spot" or readjust it with an altered standard.

From the perspective of FIG. 3 in conjunction with the schematic top view in FIG. 2, the processing line 10 with sections 11 to 14 shown in the embodiment becomes particularly clear. In FIG. 3 the separating device 2 is not shown. On the conveyor 21 can be seen a first station staffed with personnel, in which the edible products 7 to be processed, that is, the poultry breast pieces, are prepared for loading of the inspection/evaluation device 3. The trimming device 42 behind the inspection device 3 is operated by two operators (trimmers) 421. The trimming station has four work positions, two of which are occupied. The separator device 41 is in operation with ejector arms 410 which are assigned to the occupied trimming station. By control via the coupling circuit 33, the defective edible products 72 are guided into receptacles 422 by correct control with regard to time and place by means of the arms 410 which engage transversely in the product stream. On trimming tables 423 the trimmers 421 separate the defective residues and guide the products recovered in this way for transport into the middle row of the conveyor of section 14. Such alignment is only an example; the trimmed products can also be realigned in a row from which they have been taken. In FIG. 3 an intermediate check station following the trimming device 42 is not staffed, while an end station for final checking is staffed with two persons. From this end station the edible products, i.e. the filleted poultry breast pieces, are delivered to the size-sorting device 6 not shown in FIG. 3.

According to the invention stations which like the trimming stations in FIG. 3 are operated by personnel, but also other processing before and after the inspection device 3, can therefore be automated upstream or downstream and controlled by the inspection device 3 in accordance with measurement and evaluation results of the latter. This is illustrated with the aid of FIG. 4.

Figure 4:
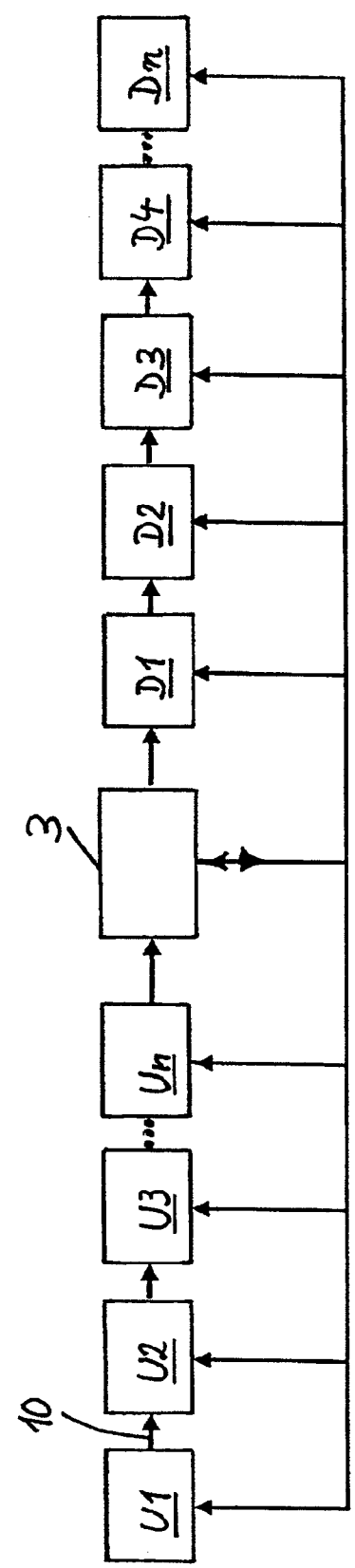

In FIG. 4 along a processing line 10 are shown processing stations U1, U2, U3, . . . Un above the inspection/evaluation device 3 as well as processing stations D1, D2, D3, D4, . . . Dn downstream. Here, Un and Dn each stand for a free number.

In the embodiment station U1 is to represent a slaughter station for poultry, station U2 represents the separating device 2 during deboning as in the practical example described above, and station U3 can be a station for removing an outer layer from the edible product to be processed.

The stations U1, U2, U3, . . . Un are each connected in a feedback circuit to the inspection/evaluation device 3, while the stations D1, D2, D3, D4, . . . Dn are each connected in a forward circuit to the inspection/evaluation circuit 3.

In conjunction with "sweet spot" control according to the invention by means of station U2, as described with the aid of FIGS. 1 to 3, the slaughter operation can also be optimised. Thus the inspection/evaluation device 3 not only determines the "sweet spot", but it is also detected with the device 3 whether blood residues which can arise from destroyed blood vessels during slaughter appear in the anatomical region of the wishbone residues in the poultry breast piece. Also, the properties of the wishbone residues are determined with the device 3. The appearance of blood residues and/or shattered wishbone residues is due to the fact that the slaughter operation is unsatisfactory, for example due to lack of stunning. The results found with the inspection device 3 are now used to optimise the slaughter operation of station U1.

Station U3 stands in a representative capacity for a further separation/processing step for optimising product recovery and/or quality improvement. The separation of a layer for fillet recovery can be used with respect to the area that remains after layer separation and that comes to light. If the layer which comes to light represents the degree of recovery, then appropriately by means of the inspection/evaluation device 3 the remaining layer is measured and for this a value is calculated which is used to optimise the degree of recovery for control of layer separation. Although such a process is here addressed in connection with the line for a poultry product, the significance of such processing becomes particularly clear if the products to be processed are fish fillets or other fish products which are skinned. Then, by means of the automatic inspection device the silver or fat layer that represents the degree of recovery after skinning can be measured, and at least one corresponding variable can be determined, which is appropriately used to adjust skinning in accordance with the preset variable.

Station D1 has already been described with the aid of FIGS. 1 to 3. This station is, in combination with the "sweet spot" control described, an essential measure for individually processing products which have the detected residues and for this purpose automatically taking them out of the flow of the other products.

Individual processing consists in particular in trimming the edible products determined, and appropriately also in return of the trimmed edible products to the main processing line 10. Also in this respect it is advantageous that, on the basis of "sweet spot" control according to the invention and in connection with it, post-trimming and if necessary return of the trimmed edible products are automated and controlled by the coupling circuit shown, in accordance with the edible products detected with the inspection/evaluation device 3 or the inspection results.

In FIG. 4, station D3 is intended to show automatic processing for final inspection. Thus inspections can be automated in section 14 of the embodiment according to FIGS. 1 to 3. It is also conceivable that data or values which are measured and calculated by an inspection device of station D4 and which detect defective residues which are still left over at the end, are returned to the inspection/evaluation device 3 and processed in the process computer of this device 3, in order to further optimise the separating operation in station U2. With suitable guidance and forwarding of automatically post-trimmed and returned edible products, the evaluation results of the device 3 can also be used to deliberately carry out at least one further automatic inspection with regard to post-trimmed edible pieces or a given group or batch of edible pieces and/or on detection of increased frequency by means of the device 3.

In FIG. 4 station D4 is intended to be a device which automatically portions and sorts the edible pieces, for example according to weight. For this purpose too the data determined with the inspection/evaluation device 3 can be used by determining values of the edible products concerning the product size and/or product weight with the device 3, and processing and using them for automatic control of the sorting device, for example the sorting device 6. The connections and couplings of the inspection/evaluation device 3 to the automated stations U1, U2, ... Un or D1, D2, ... Dn can, as in the example of station D3, also be such that data are passed from the stations to the device 3 in order to perform control operations with feedback of controlled/controlling stations.

It can be seen that the inspection/evaluation device 3 can be used in conjunction with performing the measurement and evaluation on the "sweet spot" to control a number of processing stations. An essential basis for this is that the inspection/evaluation device is provided according to the invention to particularly define and prepare residues that remain behind during separation for measurement and evaluation, by permitting and inducing them to a given extent.

The invention claimed is:

1. Method for processing fish, poultry, or other meat products conveyed in a plurality along a processing line, the meat products containing components to be separated and edible components, the method comprising:
    separating the components to be separated from the meat products to obtain edible products, wherein tolerance residues are permitted and induced in at least some of the edible products for further processing;
    measuring an actual level of the tolerance residues in the edible products and comparing to a target level of the tolerance residues in the edible products with an automatic inspection device, and adjusting the separating step based on the comparison, wherein the target level of the tolerance residues is based at least partially on at least one of size of the meat products, processing parameters, handling methods during loading, or species of the meat products; and
    separating edible products discharged from the automatic inspection device as being residue-free from edible products discharged from the automatic inspection device as having tolerance residues.

2. Method according to claim 1, further comprising manually trimming the tolerance residues from the edible products having tolerance residues discharged by the automatic inspection device.

3. Method according to claim 2, further comprising delivering the trimmed edible products and the residue-free edible products discharged by the automatic inspection device to a common processing line.

4. Method according to claim 3, further comprising manually inspecting for the tolerance residues and manually trimming the tolerance residues in a region of the common processing line.

5. Method according to claim 3, further comprising manually or automatically performing a final inspection for tolerance residues at an end of the common processing line.

6. Method according to claim 1, further comprising:
    measuring, with the automatic inspection device, at least one texture representing tolerance residues, and if necessary at least one further substance texture of the edible products,
    determining at least one variable which represents qualitative, quantitative and/or local texture substance information of the edible products, and
    using the at least one variable to influence at least one separating process in front of and if necessary at least one further processing step in front of and/or behind the automatic inspection device.

7. Method according to claim 6, further comprising determining one or more textures to be inspected or texture areas to be separated by tolerance residues which contain at least one of bones, gristle, blood vessels, fat, skin, membranes, bubbles, sinews, tissues, parasites, inclusions, structure/substance abnormalities, or foreign bodies.

8. Method according to claim 6, further comprising determining one or more textures to be inspected by at least one meat area, at least one layer area, at least one bone area and/or a structure combining such areas.

9. Method according to claim 6, further comprising predetermining at least one reference variable and/or ratio of reference variables in order to set a standard to influence at least one meat processing step.

10. Method according to claim 9, further comprising determining the at least one reference variable and/or ratio of reference variables according to characteristics of the meat product, edible product to be processed, and/or according to processing parameters.

11. Method according to claim 6, further comprising determining with the automatic inspection device at least one variable representing a degree of edible product recovery and optimizing recovery, by using the variable representing the degree of edible product recovery to control processing before the automatic inspection device to optimize the variable.

12. Method according to claim 11, wherein the meat products comprise fish products which are skinned, further comprising:
measuring a silver or fat layer of the fish products with the automatic inspection device, the silver or fat layer representing the degree of edible product recovery;
determining at least one variable corresponding to the silver or fat layer; and
using the at least one variable to adjust skinning.

13. Method according to claim 6, further comprising determining at least one texture information variable to minimise the tolerance residues during separation of the components to be separated from the meat products.

14. Method according to claim 13, further comprising determining at least two texture information variables, and comparing the at least two texture information variables to minimise the tolerance residues, at least one given ratio being preset to induce minimised tolerance residues.

15. Method according to claim 14, further comprising determining a first texture information variable representing the tolerance residue, and a second texture information variable defined by an area which is at least partially free from tolerance residues on an edible product with minimised tolerance residues.

16. Method according to claim 15, further comprising:
defining with respect to one kind of meat product, an optimal ratio of average edible meat value to average tolerance residue value for optimizing the separating process.

17. Method according to claim 6, further comprising automatically separating edible products with tolerance residues discharged by the automatic inspection device from residue-free edible products discharged by the automatic inspection device by controlling a separator device which extracts edible products with tolerance residues from a stream of inspected edible products.

18. Method according to claim 17, further comprising discharging the inspected edible products by the automatic inspection device in at least one row and preferably in two parallel rows.

19. Method according to claim 18, further comprising trimming extracted edible products with tolerance residues to separate the tolerance residues, and returning the trimmed edible products to the processing line in at least one row.

20. Method according to claim 6, further comprising automatically trimming edible products with tolerance residues to separate the tolerance residues, by the automatic inspection device controlling a trimming device.

21. Method according to claim 1, further comprising separating the tolerance residues from the meat products with an automatic separating device, and using variables measured or determined by the automatic inspection device in a feedback circuit to control the automatic separating device to minimise the tolerance residues.

22. Method according to claim 1, further comprising processing front halves of poultry or breast caps, inspecting separated fillets with the automatic inspection device, measuring a fraction of wishbones remaining as the tolerance residue and a fraction of rib meat remaining as edible meat, and setting a ratio between the fraction of wishbones to the fraction of rib meat to optimise the separating process.

23. Method according to claim 1, further comprising optimizing slaughter processing by measuring for tolerance residues and blood with the automatic inspection device in an anatomical region of the edible products, and detecting properties of the edible products which are influenced in the anatomical region by slaughter processing.

24. Apparatus for processing fish, poultry, or other meat products conveyed in a plurality along a processing line, comprising:
a separating device that separates components to be separated from the meat products to produce edible products, the separating device including at least one separating tool;
an automatic inspection device located downstream from the separating device, wherein the automatic inspection device checks the edible products for tolerance residues; and
a separator device located downstream from the automatic inspection device, wherein the separator device separates residue-free meat products from meat products having the tolerance residues distinguished by the automatic inspection device;
wherein the automatic inspection device has at least one measuring and control device that compares the actual and target values for the tolerance residues according to claim 1, which actual tolerance residues are left behind in at least some of the edible products by the separating tool, and the measuring and control device is adapted to generate at least one variable for control of at least one separating-processing step upstream of the automatic inspection device.

25. Apparatus according to claim 24, wherein the at least one measuring and control device of the automatic inspection device is adapted to measure at least one substance texture area of the edible products arising due to the tolerance residues and to generate a corresponding variable, at least one substance texture area being recognisable in particular by tolerance residues which comprise bones, gristle, blood vessels, fat, skin, membranes, bubbles, sinews, tissues, parasites, inclusions, structure/substance abnormalities, and foreign bodies.

26. Apparatus according to claim 24, wherein the at least one measuring and control device of the automatic inspection device is adapted to measure at least one texture of the edible products as well as to generate a corresponding variable, the texture being recognisable by at least one meat area, at least one layer area, at least one bone area and/or a structure combining such areas.

27. Apparatus according to claim 24, wherein the at least one measuring and control device is adapted to generate at least one variable representing the measurement result for the control of at least one further processing step upstream and/or downstream of the automatic inspection device.

28. Apparatus according to claim 27, wherein the at least one measuring and control device of the automatic inspection device generates a control variable and/or control variables which are determined by at least one ratio, for control of at least one processing step according to at least one standard, which are determined by characteristics of the meat products or edible products to be processed and/or processing parameters.

29. Apparatus according to claim 27, wherein the at least one measuring and control device of the automatic inspection device is adapted to detect tolerance residues and an area of the edible products which is at least partially free from tolerance residues for control of the separating device before the automatic inspection device to minimize tolerance residues left behind.

30. Apparatus according to claim 29, wherein the measuring and control device comprises an X-ray measuring device and an optical measuring device.

31. Apparatus according to claim 24, wherein the separating device in front of the automatic inspection device is equipped with at least one separating tool that can be controlled by the automatic inspection device, and the automatic inspection device is connected in a feedback circuit to the separating device to minimise the tolerance residues in accordance with a comparison of nominal and actual values.

32. Apparatus according to claim 24, wherein the separator device behind the automatic inspection device has, for separating edible products with and without the tolerance residues, the separator tool that extracts edible products with tolerance residues from the inspected stream of edible product.

33. Apparatus according to claim 32, wherein the separator device behind the automatic inspection device is arranged and designed for the separation of the tolerance residues in conjunction with at least one trimming device which receives edible products with residues which are separated by the separator device and makes them available after trimming for return to the processing stream of the apparatus.

34. Apparatus according to claim 33, wherein the separator device is equipped with a device that automatically separates the tolerance residues.

35. Apparatus according to claim 34, wherein the separator device is connected by a coupling circuit to the automatic inspection device in such a way that trimming takes place in accordance with at least one property of the tolerance residues, meat products and/or edible products which is detected by the automatic inspection device.

* * * * *